(12) United States Patent
Eyrard et al.

(10) Patent No.: US 11,986,581 B2
(45) Date of Patent: May 21, 2024

(54) METHOD, FACILITY AND TANK FOR THE MANUFACTURE OF A LIQUID ACID CONCENTRATE USED FOR HEMODIALYSIS MACHINES

(71) Applicant: FRESENIUS MEDICAL CARE DEUTSCHLAND GMBH, Bad Homburg (DE)

(72) Inventors: Thierry Eyrard, Lyons (FR); Philippe Laffay, Sainte-foy-les-Lyon (FR); Benoit Luaire, Sourcieux-les-Mines (FR)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 848 days.

(21) Appl. No.: 16/461,822

(22) PCT Filed: Nov. 16, 2017

(86) PCT No.: PCT/EP2017/079446
§ 371 (c)(1),
(2) Date: May 17, 2019

(87) PCT Pub. No.: WO2018/091585
PCT Pub. Date: May 24, 2018

(65) Prior Publication Data
US 2019/0358386 A1    Nov. 28, 2019

(30) Foreign Application Priority Data
Nov. 21, 2016   (FR) ...................................... 1661283

(51) Int. Cl.
*A61M 1/16*    (2006.01)
*A61K 9/08*    (2006.01)
(Continued)

(52) U.S. Cl.
CPC ............. *A61M 1/1656* (2013.01); *A61K 9/08* (2013.01); *A61K 33/14* (2013.01); *B01F 21/02* (2022.01);
(Continued)

(58) Field of Classification Search
CPC .............................. A61M 1/1656; B01F 25/50
See application file for complete search history.

(56) References Cited

U.S. PATENT DOCUMENTS

| 5,511,875 | A   | 4/1996  | Jonsson et al. |
| 5,972,223 | A * | 10/1999 | Jonsson ................ A61M 1/167 210/417 |

(Continued)

FOREIGN PATENT DOCUMENTS

| DE | 10100462 A1   | 7/2002  |              |
| DE | 10313965 B3 * | 10/2004 | .......... A61M 1/1656 |

(Continued)

OTHER PUBLICATIONS

International Search Report and Written Opinion issued in corresponding International Patent Application No. PCT/EP2017/079446 dated Feb. 23, 2018 (11 pages).

*Primary Examiner* — Elizabeth Insler
(74) *Attorney, Agent, or Firm* — Kilyk & Bowersox, P.L.L.C.

(57) ABSTRACT

A water source, an acid source, an electrolyte tank containing a mixture of electrolytes in exactly the quantity needed for the manufacture of the liquid acid concentrate, and a sodium chloride source are connected to a mixing tank. A quantity of water needed for the manufacture of the batch of liquid acid concentrate is introduced into the mixing tank. A quantity of acid needed for manufacture of the liquid acid concentrate is introduced into the mixing tank, the solution is stirred until a homogeneous solution is obtained. Part of the solution contained in the mixing tank is transferred into (Continued)

Figure 1:
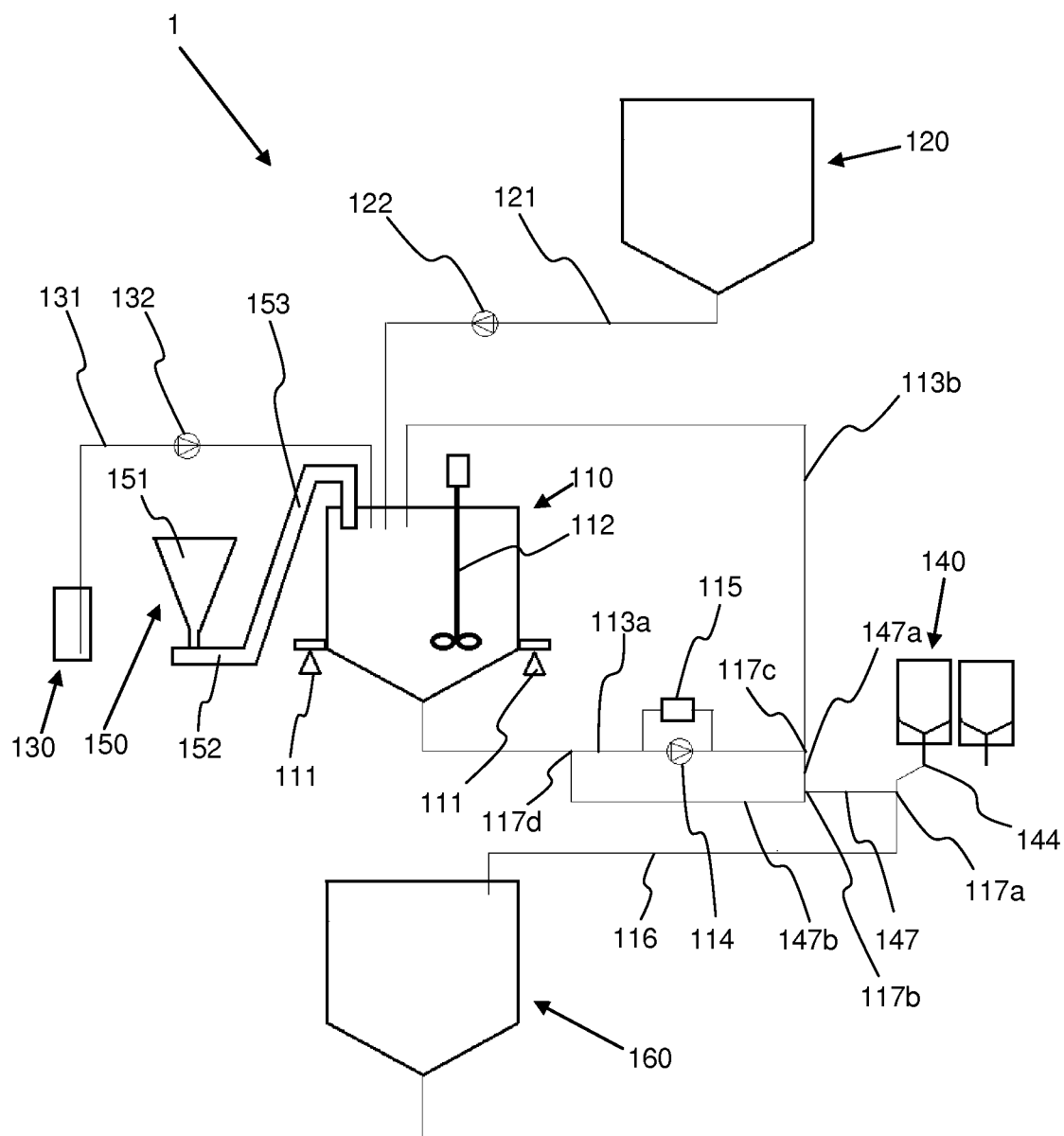

the electrolyte tank, then the solution contained in the electrolyte tank is transferred into the mixing tank. A quantity of sodium chloride needed to manufacture the liquid acid concentrate is introduced into the mixing tank. The solution is stirred and recirculated until a homogeneous liquid acid concentrate is obtained.

11 Claims, 9 Drawing Sheets

(51) Int. Cl.
| | | |
|---|---|---|
| *A61K 33/14* | (2006.01) | |
| *B01F 21/00* | (2022.01) | |
| *B01F 21/10* | (2022.01) | |
| *B01F 23/53* | (2022.01) | |
| *B01F 25/50* | (2022.01) | |
| *B01F 25/52* | (2022.01) | |
| *B01F 35/21* | (2022.01) | |
| *A61K 9/00* | (2006.01) | |
| *B01F 23/50* | (2022.01) | |

(52) U.S. Cl.
CPC .............. *B01F 21/10* (2022.01); *B01F 23/53* (2022.01); *B01F 25/50* (2022.01); *B01F 25/52* (2022.01); *B01F 35/2117* (2022.01); *B01F 35/2133* (2022.01); *B01F 35/2134* (2022.01); *A61K 9/0019* (2013.01); *A61M 2205/3393* (2013.01); *B01F 21/30* (2022.01); *B01F 23/511* (2022.01); *B01F 23/56* (2022.01)

(56) References Cited

U.S. PATENT DOCUMENTS

| | | | |
|---|---|---|---|
| 2013/0183389 A1* | 7/2013 | Carlsson | ................ A61K 33/06 |
| | | | 424/678 |
| 2014/0018727 A1* | 1/2014 | Burbank | ............ A61M 1/1672 |
| | | | 604/28 |

FOREIGN PATENT DOCUMENTS

| | | |
|---|---|---|
| DE | 10313965 B3 | 10/2004 |
| DE | 102009031473 A1 | 1/2011 |
| EP | 2886139 A1 | 6/2015 |
| FR | 2647349 A1 | 11/1990 |

* cited by examiner

METHOD, FACILITY AND TANK FOR THE MANUFACTURE OF A LIQUID ACID CONCENTRATE USED FOR HEMODIALYSIS MACHINES

This application is a National Stage Application of PCT/EP2017/079446, filed Nov. 16, 2017, which claims priority to French Patent Application No. 1661283, filed Nov. 21, 2016.

The invention concerns a liquid acid concentrate production facility for hemodialysis machines, a method for manufacturing of such a liquid acid concentrate and a tank for a dry concentrate to be used in the facility according to the invention.

Bicarbonate hemodialysis is at the present time used almost exclusively for the treatment of chronic renal failure. Each session requires between 120 and 180 l of dialysate. Alkali and alkaline-earth metals contained in the dialysate, i.e. potassium, magnesium and calcium, form salts with low solubility when mixed with carbonate. Dialysate is therefore not very stable. That is why it is common for this solution to be prepared from concentrates on site extemporaneously by the treatment machine. It is necessary to provide for a liquid basic concentrate and a liquid acid concentrate. Liquid basic concentrate is generally composed exclusively of sodium bicarbonate, whereas liquid acid concentrate contains the other constituents necessary for hemodialysis.

The basic concentrate is generally a dry concentrate. The hemodialysis machine prepares the liquid basic concentrate (a saturated bicarbonate solution) in line from the dry concentrate. It is therefore not necessary for the dry basic concentrate to be completely dissolved at the start of treatment.

The acid concentrate, however, is generally in the form of a liquid concentrate. The liquid acid concentrate is made up of several components. The key constituent is sodium chloride (about 75% by weight), then the other electrolytes (magnesium, potassium and calcium), sugar (about 22% by weight) and an acid.

The sodium, magnesium, calcium and potassium content in the dialysate must be strictly adhered to, as a variance in any of the concentrations could cause very serious side effects. The composition of the liquid acid concentrate, especially that of the Mg, K and Ca electrolytes, is therefore very important. Care must be taken to ensure they are completely solubilized. That is why the liquid acid concentrates are manufactured in high-volume batches, not by the hemodialysis machine, but in specialized manufacturing facilities that can allow for reliable and economical quality control.

As one hemodialysis session requires 3 to 5 liters of liquid acid concentrate, attempts have been made to manufacture the liquid acid concentrate on site as well, in order to avoid transporting water and to minimize costs.

This is how we know about the state of the art manufacturing facilities that allow the manufacture of liquid acid concentrate from dry concentrates or other precursor formulations. In order that they may be spread out over the entire territory near hemodialysis centers, these facilities should be limited in size and must be able to manufacture batches of 1,000 to 5,000 liters.

A first solution would be to weigh each solid component separately on site and to mix them in a mixing tank. The disadvantage is that this solution requires very complex monitoring to ensure the correct composition of the concentrate.

An improvement is to use pre-dosed bags of each solid component and to put them into solution on site. The potential for confusion is significant when using pre-dosed bags, so that every batch needs to be precisely monitored analytically.

These methods would require costly personnel expenses.

Hence, manufacturing facilities have been developed that use interchangeable containers that contain all the components of the liquid acid concentrate in the desired proportions.

In document DE 101 00 462 A1, the components of the acid concentrate are encased in a cartridge and already partly solubilized in water, the sodium chloride in particular remaining in solid form. The cartridge is connected to a mixing tank. Water is fed into the tank, passing through the cartridge until reaching a level sensor. The water supply then stops and the solution is circulated from the bottom of the tank, through the cartridge and back to the top of the tank until all of the different components, particularly the sodium chloride, are completely dissolved. The level sensor is also designed to act as a conductivity sensor. The liquid acid concentrate is ready when the conductivity of the solution reaches the desired value. Using such cartridges filled with partially dissolved components, the volume and weight of the components needing transport and storage equal only one third to one sixth of finished liquid concentrates.

In document DE 103 13 965 B3, an interchangeable container encasing all of the components of the dry acid concentrate (thus without water) is connected to a mixing tank. A predefined volume of water, measured by a flow meter, is introduced into the mixing tank and the initial water density is measured for reference. The water is circulated from the bottom of the tank, through the interchangeable container and back to the top of the tank. The water circulating inside the container causes the dry concentrate to dissolve. The density of the solution is measured to monitor the progress of component dissolution. When the dry concentrate is completely dissolved, the density of the solution should equal the control value. Using a vacuum pump system, the interchangeable container contents are sucked up and introduced into the mixing tank. The quality of the dialysate depends on the quality of the dry acid concentrate in the interchangeable container, the accuracy of the flow meter measuring the water volume and the accuracy of the density meter.

Likewise, document DE 10 2009 031 473 A1 presents an interchangeable container encasing all of the components of the acid concentrate, in either solid or partly dissolved form. The method is monitored solely by using a water meter to measure the volume of water introduced.

The disadvantage of these methods is that each component must be weighed beforehand in the cartridge or in the interchangeable container. In addition, dry acid concentrates, and even more so liquid acid concentrates, have proven to be unstable at times as the glucose reacts with the acid. Cartridges or interchangeable containers encasing all of the components of the acid concentrate cannot be stored for prolonged periods of time.

The invention's first goal is to propose compact facilities for the manufacture of liquid acid concentrate for hemodialysis machines that can be spread out over the entire territory, so they can be located near hemodialysis centers. Another goal is to manufacture a liquid acid concentrate from components which are as far as possible solid, so that no water, or as little water as possible, must be transported to the liquid acid concentrate manufacturing facility, thus limiting raw material transport and storage costs. The third goal is to appeal as far as possible to raw material providers that are within proximity to the liquid acid concentrate manufacturing facilities. A fourth goal is to propose a facility and a method allowing the monitoring of the process throughout the different steps without the use of sophisticated measurement instruments. The fifth goal is to propose a method and a facility that allow the use of constituents that are stable over time. The facility and the method should be able in particular to manufacture batches of at least 100 l, preferably at least 1,000 l.

These goals are reached through the invention's method, facility and exchangeable tank.

The invention's method for manufacturing a predetermined quantity of a batch of liquid acid concentrate for hemodialysis machines consists of the following steps:

Preliminary step: connection to a mixing tank of
- a water source,
- an acid source,
- a sodium chloride source and
- an electrolyte tank containing a mixture of the electrolytes potassium and/or calcium and/or magnesium in exactly the quantity needed for the manufacture of the batch of liquid acid concentrate, wherein said electrolyte mixture may contain, in addition, at most one part of the acid and/or at most one part of the sodium chloride needed for the manufacture of the batch of liquid acid concentrate;

Step a): Introduce the quantity of water needed to manufacture of the batch of liquid acid concentrate into the mixing tank;

Step b): Introduce the quantity of acid needed to manufacture the batch of liquid acid concentrate into the mixing tank, taking into account the quantity of acid that may be present in the electrolyte tank;

Step c): Repeat following sub-steps until the electrolyte mixture contained in the electrolyte tank is completely dissolved: Sub-step c1) transfer part of the solution contained in the mixing tank into the electrolyte tank, then Sub-step c2) transfer the solution contained in the electrolyte tank into the mixing tank, leaving the still solid constituents in the electrolyte tank;

Step d): Introduce the quantity of sodium chloride needed to manufacture the batch of liquid acid concentrate into the mixing tank, taking into account the quantity of sodium chloride that may be present in the electrolyte tank;

Step e): Stir and recirculate the solution by taking it from a point in the mixing tank and reintroducing it at another point until a homogeneous liquid acid concentrate is obtained; wherein Steps a) to d) can be performed in any order, Step a) preceding always Step c).

It is preferable that the quantity of water, acid and sodium chloride introduced into the mixing tank in Steps a), b) and d) be determined by weighing, in particular by means of a scale integrated into the mixing tank.

It is preferable that during Sub-steps c1) and c2) the quantity of solution transferred from the mixing tank into the electrolyte tank be weighed, and/or that the quantity of solution transferred from the electrolyte tank into the mixing tank be weighed. This allows the progress of the electrolyte mixture dissolution to be monitored. Between the start and the end of Step c), the weight of the solution must have increased by the weight of the solid electrolyte mixture initially contained in the electrolyte tank. It is preferable that weighing be performed by means of a scale integrated in the mixing tank.

For faster dissolution and homogenization, it is preferable that the solution contained in the mixing tank be stirred during all of Steps b) to e) with stirring means, preferably with a stirrer with mechanical drive. The stirring can, however, be stopped, for example to take measurements.

For quality control of the process, the conductivity of the solution contained in the mixing tank can be measured during and/or at the end of Step b) and compared to a control value, and the solution can be homogenized in Step b) until the measured conductivity corresponds to the control value. When the solution is homogeneous at the end of Step b), the conductivity of the solution must correspond with the control value. The conductivity value is a reliable indicator for monitoring the end of Step b). For example, conductivity measured at 25° C. may be 648 µS/cm±15 µS/cm.

Similarly, it is possible to measure the density of the solution during and/or at the end of Step e) and compare it with a control value, wherein the solution can be kept recirculating in Step e) until the density measured corresponds to the control value. If the qualitative and quantitative composition of the liquid acid concentrate is consistent, the density measured must correspond to the control value.

Sodium chloride and/or acid, if present in solid form, can be introduced by conveyors, in particular by screw conveyors, while water and/or acid and/or sodium chloride, if the latter two are present in liquid form, can be introduced by means of a line equipped with a pump, which connects the relevant source to the mixing tank.

The various constituents of the liquid acid concentrate are preferably introduced at the top of the mixing tank. During Sub-step c1) it is preferable that the solution be taken from the bottom of the mixing tank and be reintroduced during Sub-step c2), preferably at the top of the mixing tank. Similarly, in Step e) it is preferable that the solution be taken from the bottom of the mixing tank and preferably reintroduced at the top of the mixing tank.

The invention also concerns a facility for manufacturing a predetermined quantity of a batch of liquid acid concentrate for hemodialysis machines. The facility includes
- a mixing tank,
- a water source that can be connected to the mixing tank via a water introduction line,
- an electrolyte tank containing a mixture of the electrolytes potassium and/or calcium and/or magnesium in the exact quantities needed to manufacture the batch of liquid acid concentrate, wherein said electrolyte mixture may contain at most one part of the acid and/or at most one part of the sodium chloride needed for the manufacture of the batch of liquid acid concentrate, said electrolyte tank can be connected to the mixing tank by a line equipped with a pump to transfer part of the solution from the mixing tank into the electrolyte tank, and a line for transferring the solution contained in the electrolyte tank into the mixing tank, and a recirculation line equipped with a pump.

According to the invention, the facility also includes
- an acid source that can be connected to the mixing tank and which can be equipped with means for introducing the quantity of acid needed for the manufacture of a batch into the mixing tank, taking into account the quantity of acid which may already be present in the electrolyte tank, and
- a sodium chloride source that can be connected to the mixing tank and which can be equipped with means for introducing the quantity of sodium chloride needed for the manufacture of a batch into the mixing tank, taking into account the quantity of sodium chloride which may already be present in the electrolyte tank.

It is preferable that the mixing tank be equipped with a scale to determine by weighing the amount of water, acid and sodium chloride introduced into the mixing tank and/or to weigh the quantity of solution transferred from the mixing tank into the electrolyte tank, as well as the quantity of solution transferred from the electrolyte tank into the mixing tank.

The mixing tank is preferably equipped with stirring means, for example a stirrer with mechanical drive such as a propeller.

For quality control during the manufacture of a batch of liquid acid concentrate, a conductivity meter is preferably provided to measure the conductivity of the solution, especially after adding the acid in Step b), wherein the conductivity meter can be placed in the mixing tank or in the recirculation line, for example. Likewise, a density meter can be provided, preferably in the recirculation line or in a bypass of the recirculation line, to measure the density of the solution during and/or at the end of Step e).

To ensure proper homogenization, the line for introducing the water into the mixing tank and/or the line for transferring the solution contained in the electrolyte tank into the mixing tank and/or the means for introducing the acid into the mixing tank and/or the means for introducing the sodium chloride into the mixing tank preferably opens into the top of the mixing tank. It is also preferable that the inlet of the line for transferring a portion of the solution from the mixing tank to the electrolyte tank be located at the bottom of the mixing tank. Likewise, it is preferable that the inlet of the recirculation line be located at the bottom of the mixing tank and the outlet of the recirculation line be located at the top of the tank.

Finally, the invention also concerns an electrolyte tank for the manufacture of a predetermined quantity of a batch of liquid acid concentrate for hemodialysis machines, wherein this electrolyte tank contains a mixture of the electrolytes magnesium and/or calcium and/or potassium in exactly the quantity needed to manufacture the batch of liquid acid concentrate. The electrolyte tank is equipped with means for connecting it to a mixing tank. In addition, the electrolyte mixture contains sodium chloride and/or acid in quantities strictly lower than those required to manufacture a batch of liquid acid concentrate. It must be understood that the mixture may contain neither sodium chloride nor acid, or that these elements may be present in insufficient quantities, therefore it is always necessary to have a source of sodium chloride and a source of acid in the facility.

In a preferred embodiment of the invention, the electrolyte mixture contains neither sodium chloride nor acid.

The electrolyte mixture may contain a sugar, in particular glucose, preferably in the quantity needed to manufacture the batch of liquid acid concentrate. Another solution would be to provide, in addition to the source of acid and the source of sodium chloride, a source of sugar with means for introduction thereof and a corresponding introduction step.

It is preferable that the electrolyte tank be equipped with a single line allowing both the transfer of the solution from the mixing tank into the electrolyte tank, as well as the transfer of the solution from the electrolyte tank into the mixing tank, the single line being equipped with a connector for connection to the line or lines used to transfer the solution from the mixing tank into the electrolyte tank and to transfer the solution from the electrolyte tank into the mixing tank.

It is preferable that the electrolyte tank consists of a flexible inner bag within a rigid casing, preferably a cardboard box.

The method for manufacturing a liquid acid concentrate, the corresponding facility and the electrolyte tank are described in more detail below with the help of the following figures:

FIG. 1 schematic representation of the facility;
FIGS. 2*a* to 2*g* The different steps of the method;
FIG. 3 Electrolyte tank.

In the example shown here, the sodium chloride is in solid form and the acid is 80% concentrated acetic acid in liquid form. However, it would be possible to use another acid, especially in solid form, such as citric acid, or a concentrated or saturated sodium chloride solution. The electrolyte mixture not only contains magnesium, potassium and calcium in the quantities needed to manufacture a batch, but also glucose. It would be conceivable to manufacture a liquid acid concentrate without glucose, or to separate glucose from the other electrolytes and to introduce it separately, as can be done for example with the acid.

The facility (1) as illustrated in FIG. 1 particularly includes:
- a mixing tank (110);
- a source of water in the form of a water tank (120);
- a source of acid in the form of an acid tank (130);
- an electrolyte tank (140);
- a source of sodium chloride in the form of a sodium chloride tank (150); and
- a buffer tank (160).

The mixing tank (110) is equipped in particular with
- a scale (111) allowing the weighing of the various components as they are added;
- stirring means (112), such as a stirrer, for example a stirrer with mechanical drive such as a propeller;
- a withdrawal line (113*a*) equipped with a pump (114) and a density meter (115) placed in a bypass of the withdrawal line, preferably between the pump inlet and outlet, in order to reduce the flow directed at the density meter;
- a return line (113*b*), the withdrawal line (113*a*) and the return line (113*b*) constituting a recirculation line;
- a transfer line (113*a*, 147*a*, 147, 116) to move the finished solution into the buffer tank (160).

The scale may comprise several, e.g. three, sensors onto which the mixing tank is placed. For example, these sensors each have sensitivity levels of ±50 g.

The withdrawal line inlet (113*a*) is preferably located at the bottom of the mixing tank, while the return line (113*b*) preferably opens into the top of the mixing tank. The recirculation line makes it possible to take the solution from the bottom of the tank and reintroduce it at the top of the tank in order to improve solution homogenization.

Each tank (120, 130, 140, 150) can be connected to a means of introducing the product to be added from the corresponding tank into the mixing tank (110). The means of introduction may be lines equipped with pumps if the product to be added is liquid, or other means for introduction, such as screw conveyors, for solid products.

The water tank (120) contains water suitable for producing liquid acid concentrate for hemodialysis, such as purified water. It can be connected to a water introduction line (121) which makes it possible to introduce water from the tank (120) into the mixing tank (110), preferably into the top of the tank. A pump (122) may be provided in the water introduction line.

The acid tank (130) contains the acid to be added to the solution. The acid may be solid, e.g. citric acid, or liquid. In the figures shown here, the acid used is 80% concentrated acetic acid. Concentrated acetic acid is usually supplied in 200 l drums or in 1,000 l containers. The acid tank (130) can be connected to an acid introduction line (131) which opens into the mixing tank, preferably in the top of the tank. When connected, the inlet of the acid introduction line is preferably located at the bottom of the acid tank. A pump (132) can be provided in the line (131) to bring acid from the acid reservoir to the mixing tank. If the acid is in solid form, the introduction line must be replaced by other suitable means for introduction, such as a screw conveyor.

The electrolyte tank (140) contains a mixture of different electrolytes, particularly magnesium (Mg), potassium (K) and calcium (Ca) in the form of magnesium chloride ($MgCl_2$), potassium chloride (KCl) and calcium chloride ($CaCl_2$), as well as glucose. The proportion of electrolytes in the ready-to-use liquid acid concentrate is paramount for patient safety. It is therefore preferable to use a ready-made mixture, prepared in specialized production facilities that manufacture in line a mixture which is generally found in granulate form. One may refer to document EP 0 287 978 A1 for a description of the method for continuous manufacturing of such a granulate. The different components magnesium, potassium, calcium and glucose are present in the electrolyte tank in the exact quantities needed to manufacture a batch of liquid acid concentrate. The advantage of using such a mixture lies in the fact that it requires only one weighing.

The electrolyte reservoir (140) shown in FIG. 3 as an example, is a flexible inner bag (141) within a rigid casing, such as a cardboard box (142). The inner bag (141) is equipped in its lower section with a single bag line (143) terminated by a connector (144). A filter (145) is placed upstream of the bag line (143), within the flexible bag, to prevent the not yet solubilized solid product from entering the bag line (143) and the mixing tank (110). The filter is preferably designed to serve also as a diffuser, so that the solution is introduced into the inner bag (141) in the form of a high-speed, high-power spray.

The connector (144) can be connected, via a three-way valve (117a), to an electrolyte transfer line (147) also used for the transfer of the solution from the mixing tank to the electrolyte tank and for the transfer of the solution from the electrolyte tank to the mixing tank. This electrolyte transfer line then splits into a supply line (147a) and an extraction line (147b). The supply line (147a) is connected, via a three-way valve, to the withdrawal line (113) at the connecting point between the withdrawal line (113a) and the return line (113b), and serves to transfer the solution from the mixing tank (110) into the electrolyte tank (140). The extraction line (147b) opens into the withdrawal line (113a) of the recirculation line, e.g. upstream of the pump (114). It is used to transfer the solution from the electrolyte tank (140) into the mixing tank (110).

The sodium chloride tank (150) is formed, e.g. of a hopper (151) that can be connected to one or more screw conveyors (152, 153) that bring the sodium chloride into the top of the mixing tank (110). Sodium chloride is usually supplied in the form of 25 kg bags. The bags need only be emptied into the hopper. If the sodium chloride were in solution form, it would be necessary to replace the screw conveyors with a line possibly equipped with a pump.

In the example shown here, some lines are connected to each other by three-way valves to direct the various solutions into the desired lines. Thus, the following lines are connected together by a three-way valve:

Three-way valve (117a): connector (144) for bag line (143), electrolyte transfer line (147) and transfer line (116) to the buffer tank;
Three-way valve (117b): electrolyte transfer line (147), supply line (147a) and extraction line (147b);
Three-way valve (117c): withdrawal line (113a), return line (113b) and electrolyte supply line (147a);
Three-way valve (117d): extraction line (147b) and withdrawal line (113a).

It is intended that the manufacture of a batch of liquid acid concentrate consume the entire contents of a whole number of electrolyte tanks (140). In the example shown here, a single electrolyte tank is sufficient. However, it would be conceivable to use the contents of two or more tanks for the manufacture of larger batches. The volume of the electrolyte tank (140) and the mass of its contents are therefore adapted to the volume of the batch of liquid acid concentrate to be manufactured.

Likewise, instead of providing one or more tanks containing the exact quantity of electrolytes required, this quantity then being taken from the tank(s) by successive dissolutions, it would also be possible to provide a source of the mixture in suitable proportions, and to withdraw precisely the desired quantity for each batch, this quantity being measured by weighing, as is done with the sodium chloride. To do so, it would be possible, for example, to store the mixture in a hopper and to transfer the mixture into the mixing tank using appropriate transport means such as screw conveyors.

It should be noted, however, that the solution of using one or more tanks containing the exact quantity of electrolytes to be extracted by successive dissolutions has several advantages over the solution of taking the desired quantity from a hopper. The first advantage lies in the greater precision achieved in the quantities added, which is an important criterion for patient safety. Moreover, the formulation of the electrolyte mixture is often adapted to meet patients' needs. There are therefore different possible formulations. With containers containing the exact quantity of electrolytes, no residue remains in the facility after normal cleaning. It is therefore possible to successively prepare liquid acid concentrates of different formulations without having to perform specific procedures. However, when mixing in bulk, it is necessary to provide as many hoppers and means of introduction as formulations, or to empty and clean the hopper and the means of introduction. Lastly, when the mixture contains a sugar, it is very sensitive to bio-contamination. It is therefore best to keep it in a safe place, in a closed container.

In the example presented here, the mixing tank (110) intended for the manufacture of a 4,000 l batch of liquid acid concentrate has a volume of 5,000 l, the electrolyte tank (140), with a volume of about 500 l, contains 310 kg of ready-made MgCl/KCl/$CaCl_2$/glucose mixture in suitable proportions. An acid tank (130) can be used for several batches and the NaCl hopper (151) is refilled as required, knowing that a full hopper could be enough for the manufacture of several batches of liquid acid concentrate. The water tank (120) has a volume greater than or equal to the volume required to manufacture a batch of liquid acid concentrate.

The method is described below by means of an example for the manufacture of a 4,000 l batch of liquid acid concentrate. The quantities stated and durations indicated are only examples, as the method can be used with other quantities and the duration of the different steps must be adapted to each particular case.

In a preliminary step, the different tanks (120, 130, 140, 150) are connected to the mixing tank (110).

Figure 2A:
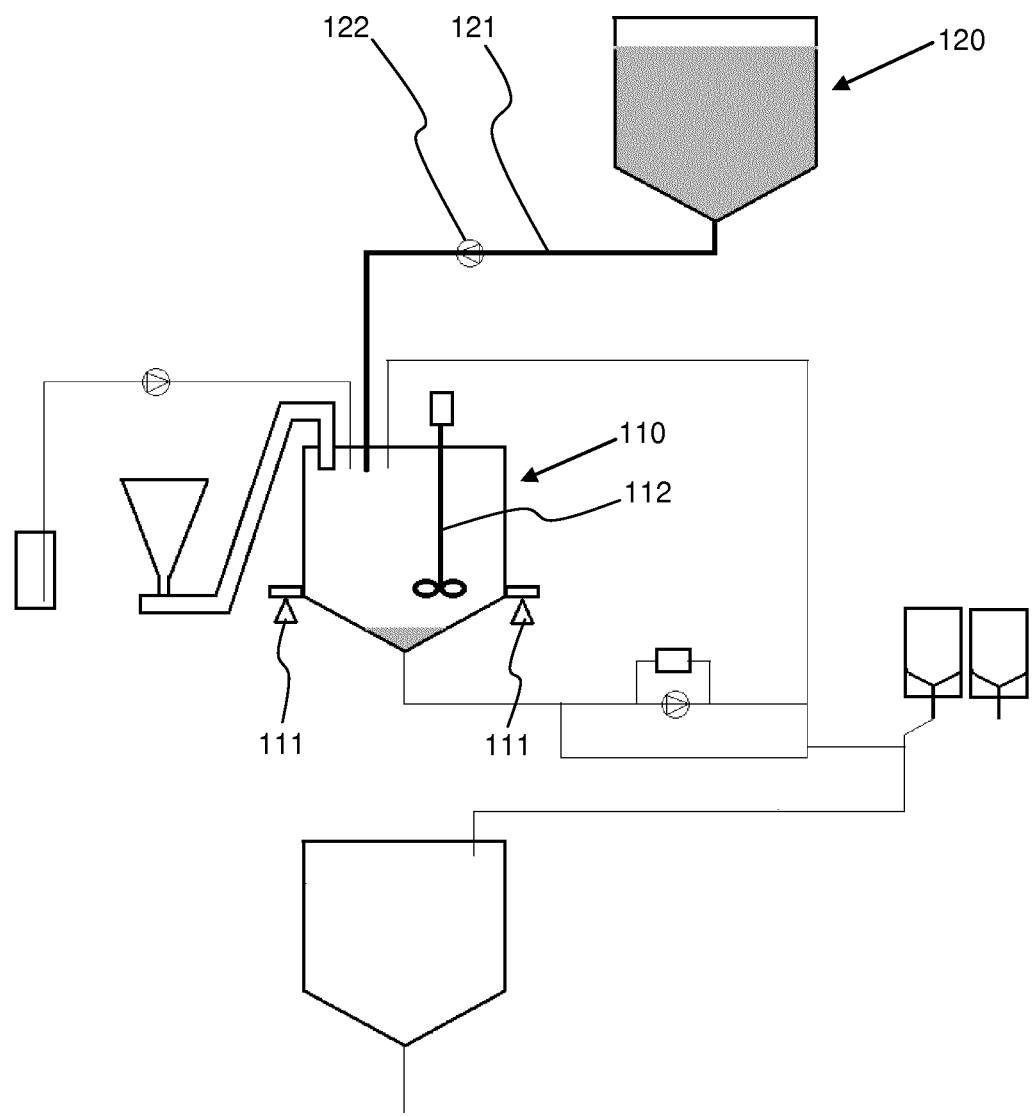
Figure 3:
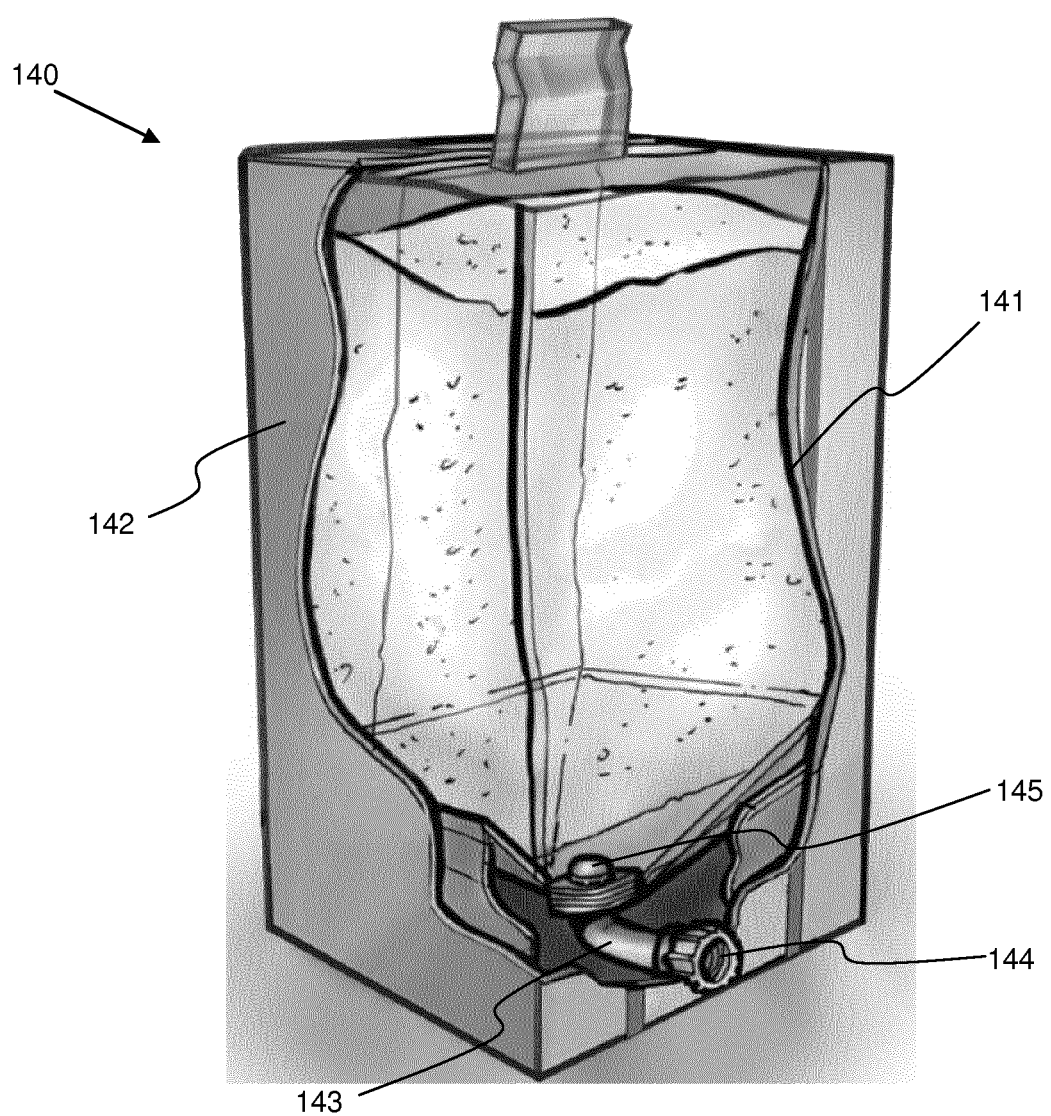

In a first step, namely Step a), which is schematically illustrated in FIG. 2a, the quantity of water required for the production of a batch (here 3,300 kg) is introduced from the water tank (120) into the mixing tank (110) via the water introduction line (121) and the pump (122). The exact quantity is determined using the mixing tank's integrated scale (111). During tests, this step took about 15 minutes.

Figure 2B:
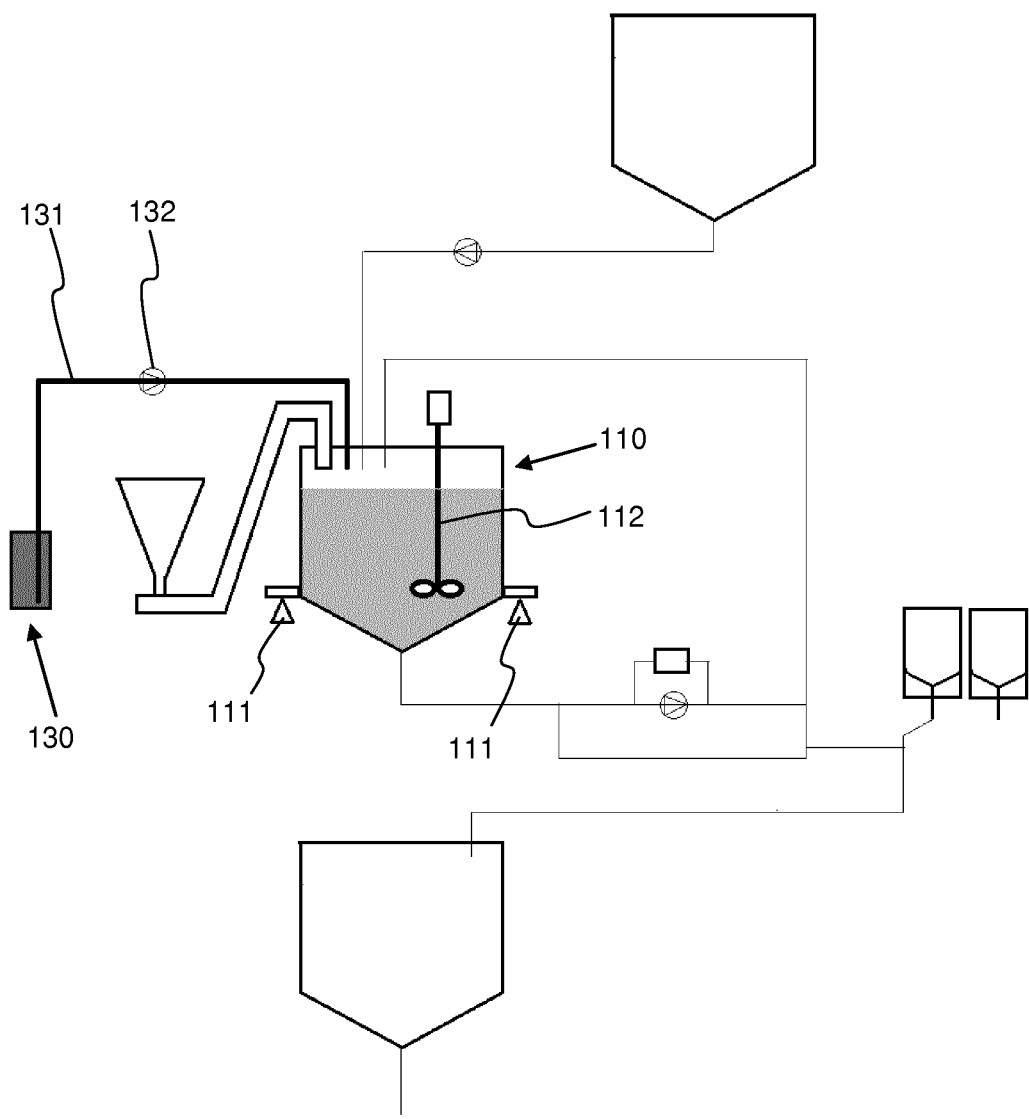

In a second step, namely Step b), which is illustrated in FIG. 2b, the acid is introduced from the acid tank (130) into the top of the mixing tank (110) via the acid introduction line (131) and the corresponding pump (132). The exact amount of acid (here 40.5 kg) is measured using the mixing tank's integrated scale (111). This step took about 10 minutes.

The mixture is still stirred, for e.g. about 2 minutes, using the stirrer (112) until a homogeneous acid solution is obtained, hereinafter referred to as "Solution B". Once stirring is complete, the conductivity of Solution B is measured to validate Step b).

Figure 2C:
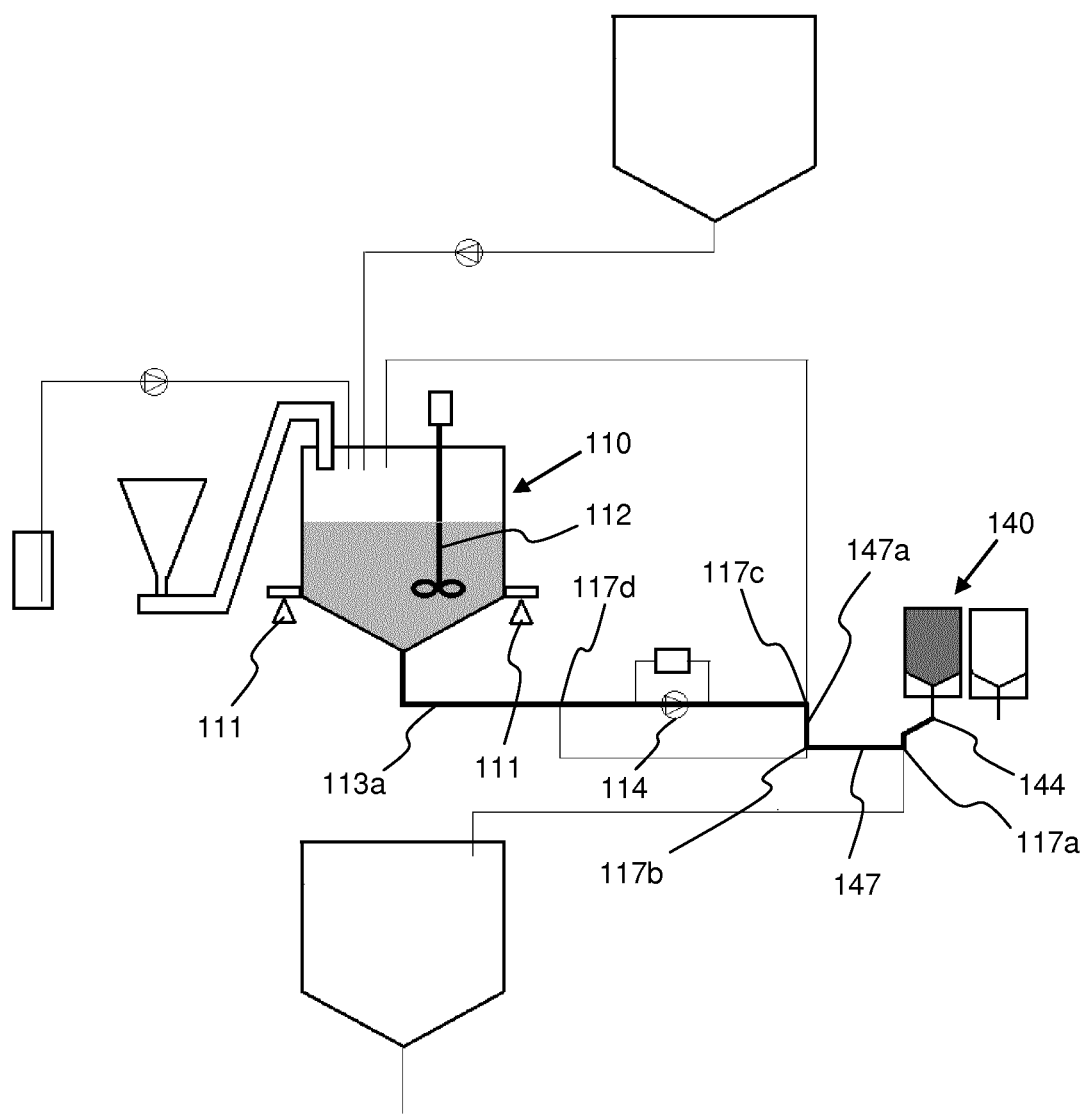
Figure 2D:
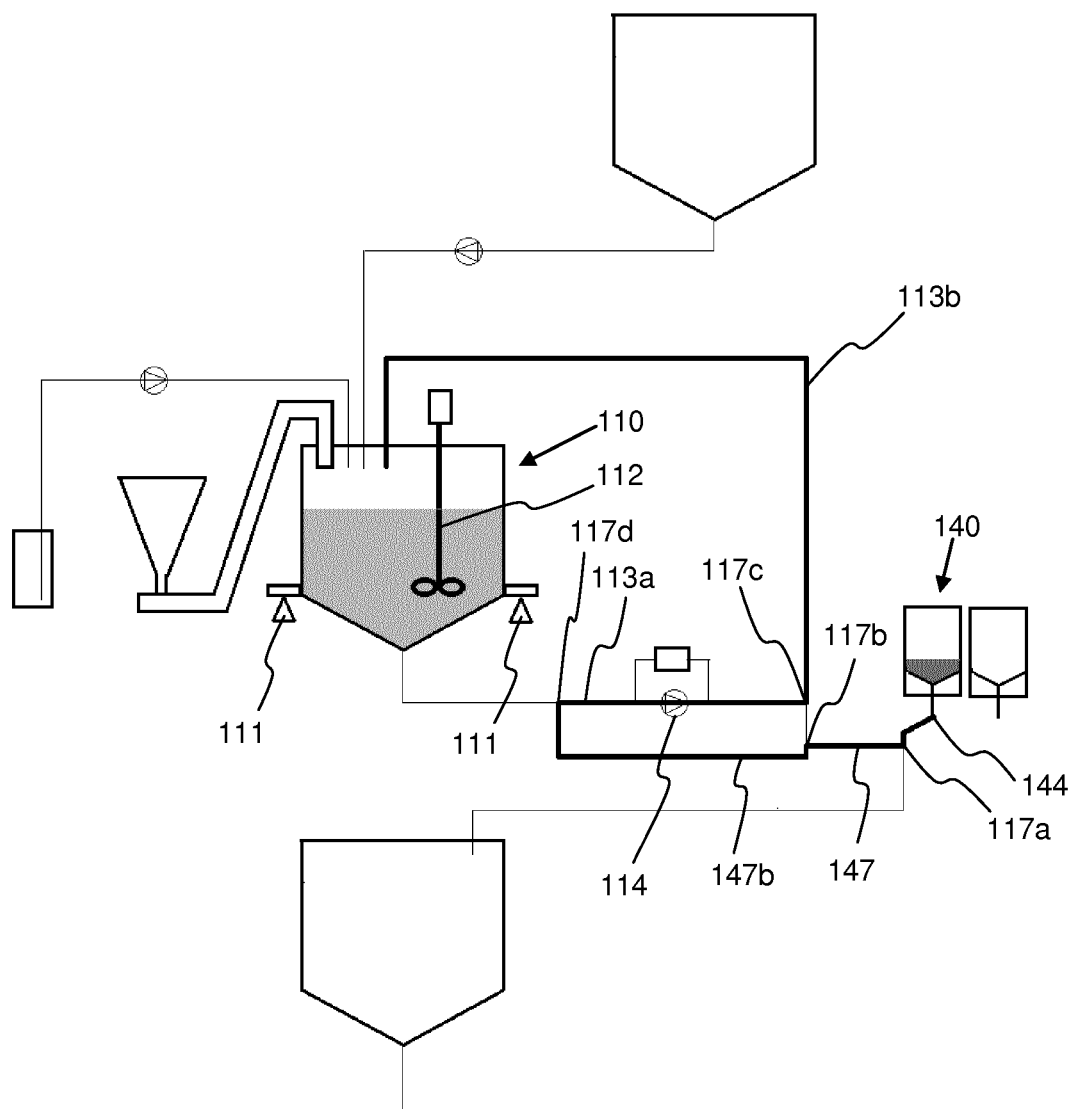

In a third step, namely Step c), illustrated in FIGS. 2c and 2d, the contents of the electrolyte tank (140) are added to Solution B.

In a first sub-step, namely Sub-step c1), illustrated in FIG. 2c, part of Solution B is taken from the bottom of the mixing tank (110) and is transferred into the electrolyte tank (140) via the withdrawal line (113a), the supply line (147a), the electrolyte transfer line (147), the three-way valve (117a), the connector (144), the bag line (143) and the filter (145) that diffuses the solution into the electrolyte mixture at high speed and with a lot of energy. The mixing tank's integrated scale (111) makes it possible to control the quantity of Solution B taken from the mixing tank and transferred into the electrolyte tank (140). The electrolyte mixture containing the glucose partially dissolves in Solution B thus transferred. In tests, the volume of solution introduced varied between 30 and 300 liters.

In Sub-step c2), schematically illustrated in FIG. 2d), the solution thus obtained is transferred into the top of the mixing tank (110) via the filter (145) which holds the undissolved solid particles, the bag line (143), the connector (144), the three-way valve (117a), the electrolyte transfer line (147), the extraction line (147b), the second part of the withdrawal line (113a), and the return line (113b). The solution in the mixing tank (110) is stirred with the stirrer (112). The weight of the solution in the mixing tank is monitored by the integrated scale (iii).

Step c) with its Sub-steps c1) and c2) are repeated several times, until the contents of the electrolyte tank (140) are completely dissolved. This state is monitored by the integrated scale (111). Between the beginning and end of Step c), the weight of the solution in the mixing tank must have increased by the weight of the electrolyte mixture initially contained in the electrolyte tank (140). Sub-steps c1) and c2) are repeated as long as the weight of the solution in the mixing tank following Sub-step c2) has not reached the theoretical weight. In tests, Step c) was repeated 15 times and lasted about 30 minutes.

Figure 2E:
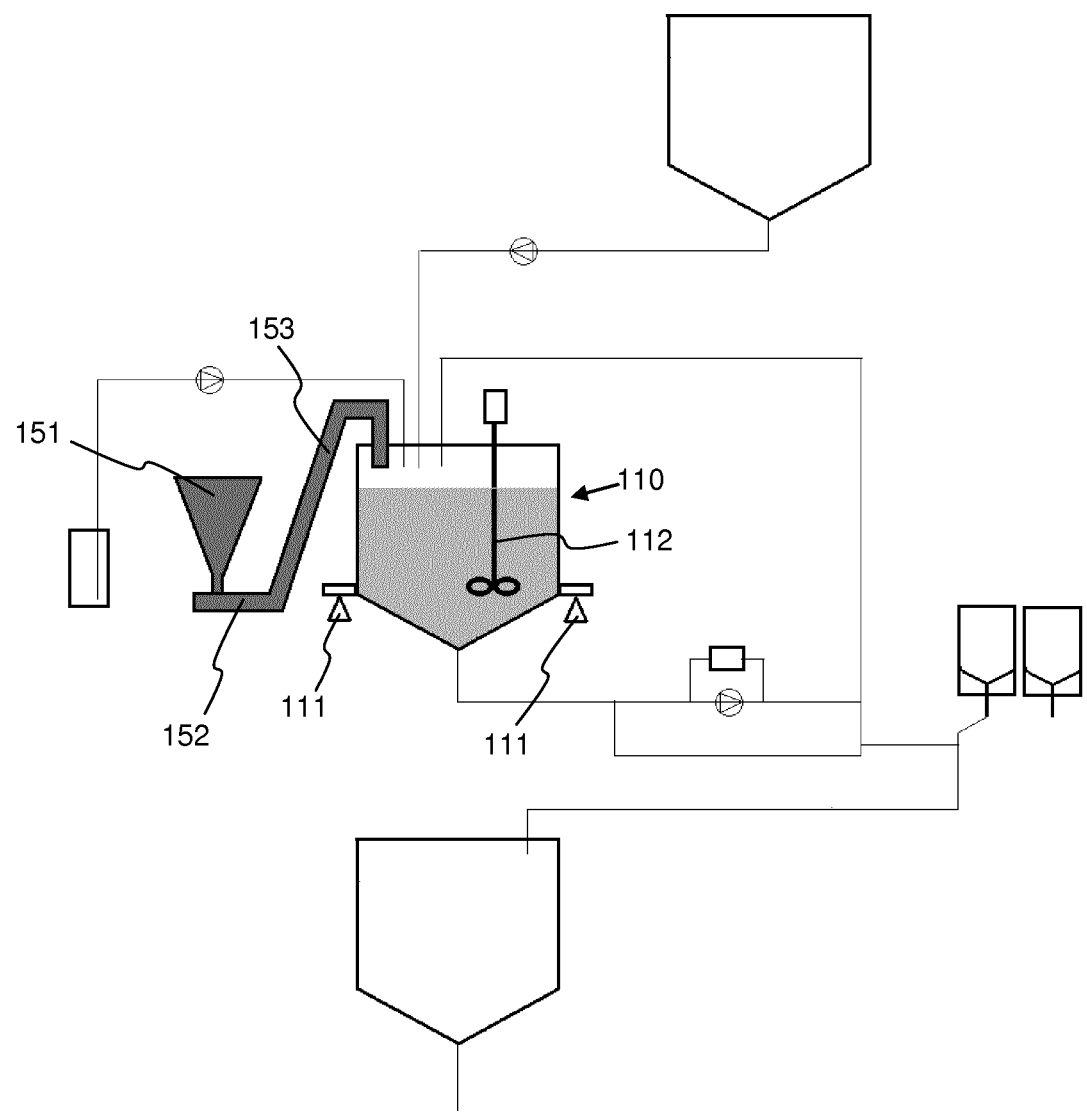

The fourth step, namely Step d), schematically illustrated in FIG. 2e, is to add sodium chloride (NaCl) to complete the liquid acid concentrate. To do so, the sodium chloride is taken from the hopper (151) and brought to the top of the mixing tank (110) via the two screw conveyors (152, 153). The exact quantity of sodium chloride, in this example 1,050 kg, is measured using the integrated scale (111). The solution is stirred until the sodium chloride is completely dissolved. During tests, this step took about 20 minutes.

It is understood that the exact order of Steps a) to d) is not of particular importance, at most it is necessary to introduce the water in Step a) before proceeding with the solubilization of the electrolyte mixture in Step c). However, the order chosen in this example allows for simple quality control monitoring of the method as it progresses.

Figure 2F:
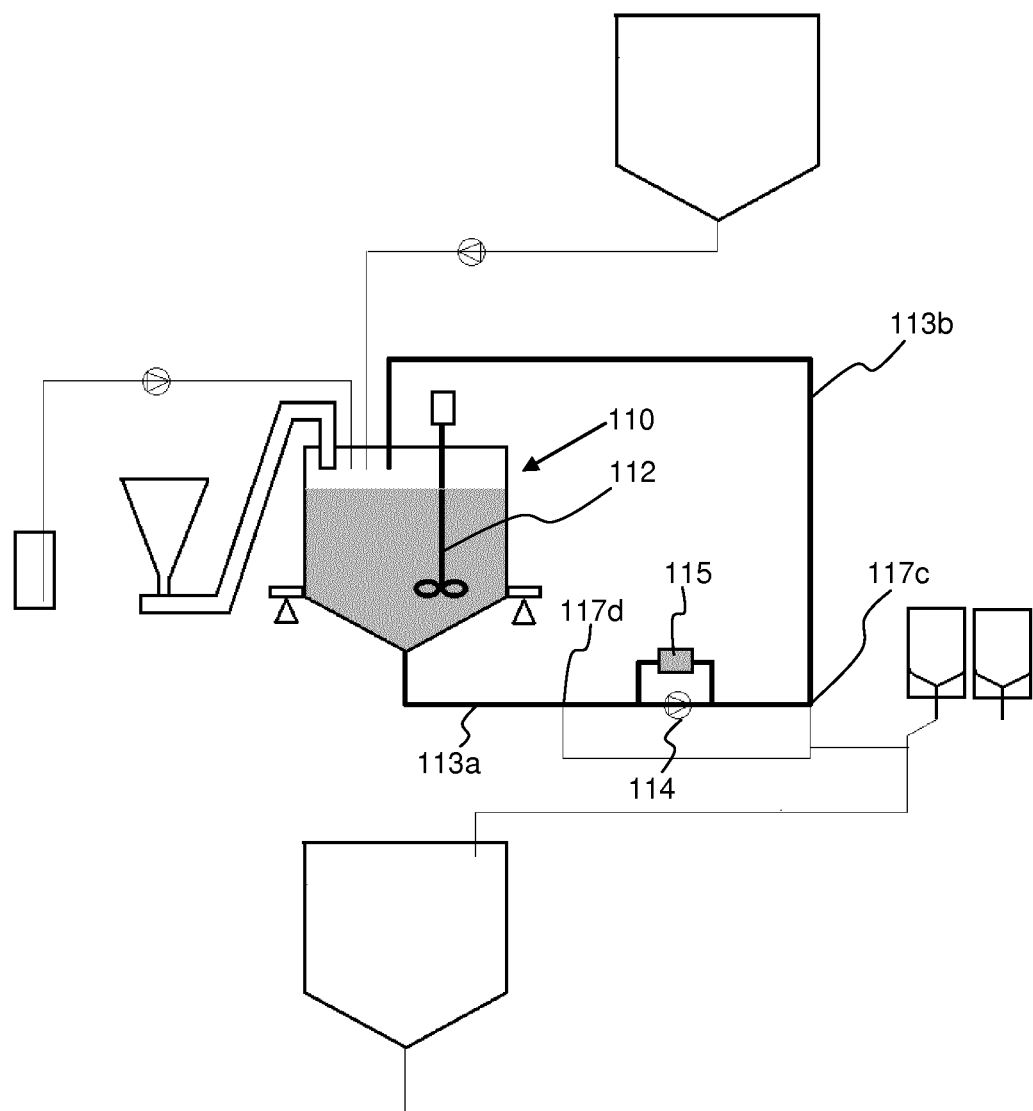
Figure 2G:
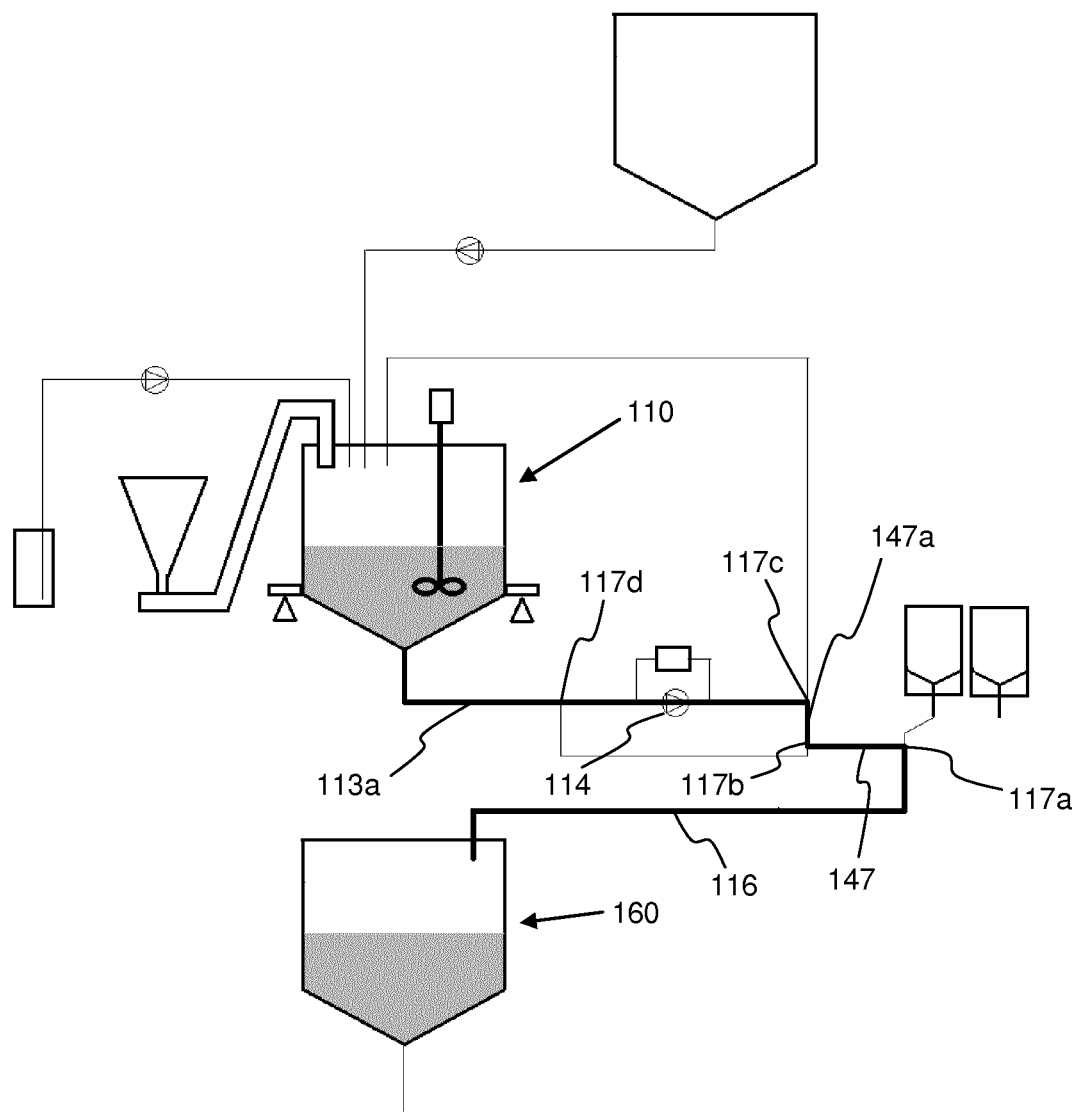

The fifth step, namely Step e), illustrated in FIG. 2f, is to homogenize the liquid acid concentrate obtained. To do so, the solution is recirculated from the bottom of the mixing tank upwards through the withdrawal line (113a) and the return line (113b) and through the density meter (115). In tests, Step e) lasted 5 minutes. This recirculation and stirring with the stirrer (112) help to homogenize the liquid acid concentrate.

At the end of Step e), the solution density must be consistent with a control value. This quality test ensures that all steps have been correctly completed. Before releasing the batch, additional chemical tests can be performed, which can preferably be performed in simple laboratories without the need for expensive and/or complicated equipment. As an example, the calcium and potassium content can be monitored using electrodes which are specific to these cations.

The liquid acid concentrate is then ready for use and can be conveyed into a buffer tank (160) by way of the conveying line. In the example shown here, this conveying line is comprised of the withdrawal line (113a), the electrolyte supply line (147a), the electrolyte transfer line (147) and the transfer line (116). This conveying process requires about 10 minutes.

Due to the layout of the different lines chosen in this example, only one pump (114) is needed
- to transfer Solution B into the electrolyte tank (140) during Sub-steps c1), then
- to transfer the solution from the electrolyte tank (140) into the mixing tank at the end of Sub-steps c1),
- to recirculate the liquid acid concentrate to homogenize it during Step e), and
- to convey the ready-to-use liquid acid concentrate into the buffer tank.

The buffer tank can be connected to a network directly feeding a hemodialysis center. It can also be connected to a packaging facility in which the liquid acid concentrate is poured into tanks which are then distributed to more distant hemodialysis centers.

It is possible for some of the sodium chloride and/or acid to already be present in the electrolyte tank, yet quantities would be insufficient for the manufacture of the liquid acid concentrate. In such cases, the quantity of acid added in Step b) and of sodium chloride added in Step d) must be reduced accordingly to maintain the desired final composition.

All objectives defined by the invention have been achieved. The installation of the invention is compact enough to allow it to be set up in many locations throughout the territory, thus greatly reducing the distances required to supply it to hemodialysis centers. Most or all of the components may be in solid form. In the example shown here, only the acetic acid contains 20% water. Using pure acetic acid (glacial acetic acid) would be more complicated and incur much higher costs than transporting acid containing 20% water. Hence, the 80% concentration is a good compromise. Moreover, the 40.5 kg of acetic acid represents a very small fraction of the added components, particularly when compared to the 1,050 kg of sodium chloride.

Sodium chloride and concentrated acetic acid (or citric acid) are common components that can be purchased locally.

Only the electrolyte mixture is a specific component that is only manufactured at specialized sites. However, its mass (310 kg) is significantly less than that of the sodium chloride (1,050 kg). Transport costs are considerably reduced by choosing this mixture separated from the sodium chloride and the acid.

The process is monitored at different stages somewhat redundantly.

The use of a scale provides much more precise monitoring than state of the art flow meters or level sensors. Moreover, unlike flow meters or level sensors, scales can be used for steps other than the initial introduction of the water.

In addition to monitoring the weight of the various components added, the conductivity of the solution can be monitored after the addition of the acetic acid. At this stage of the method, only the acid in the solution can affect the conductivity.

In addition, the density of the liquid acid concentrate is monitored to validate the end of the method.

The scale, the conductivity sensor and the density meter are accurate, reliable and resistant measuring instruments.

Additional simple chemical tests can also be performed before releasing each batch.

Lastly, separating the glucose from the acid ensures a much more stable electrolyte mixture which does contain glucose.

Many steps can be automated, which reduces staff workload. The method and the facility ensure the safety of the liquid acid concentrate composition. Using an electrolyte mixture on one side and separate components on the other allows for a high level of automation. Staff workloads are admittedly higher if three tanks must be prepared, compared to connecting an interchangeable container that contains all of the components. Overall, however, the solution proposed with the invention represents a saving in personnel because it is no longer necessary to weigh the different components upstream (at another site).

Moreover, by using a mixture of electrolytes and glucose produced in line, as detailed in EP 0 287 978 A1, only the required quantity of this mixture must be weighed in the electrolyte tank and not every component, as is necessary with the methods of the state of the art. Since the concentration of electrolytes is an essential component of the liquid acid concentrate, it is preferable in any case to prepare this mixture at specialized sites, even if it means that they will be further away than local suppliers of each of the individual components.

It would also be possible to combine in a same tank the electrolytes potassium and/or calcium and/or magnesium and the entire quantity of the sodium chloride needed for the manufacture of the batch of liquid acid concentrate. In such a case, there is no step of introducing the quantity of sodium chloride needed to manufacture the batch of liquid acid concentrate into the mixing tank, taking into account the quantity of sodium chloride that may be present in the electrolyte tank. The process runs as follows:

Preliminary step: connection to a mixing tank of
a water source,
an acid source,
an electrolyte tank containing a mixture of the electrolytes potassium and/or calcium and/or magnesium and the sodium chloride, all in exactly the quantity needed for the manufacture of the batch of liquid acid concentrate, wherein said mixture may contain, in addition, at most one part of the acid needed for the manufacture of the batch of liquid acid concentrate;

Step a'): Introduce the quantity of water needed for the manufacture of the batch of liquid acid concentrate into the mixing tank;

Step b'): Introduce the quantity of acid needed for manufacture the batch of liquid acid concentrate, taking into account the quantity of acid that may be present in the electrolyte tank, into the mixing tank;

Step c'): Repeat Sub-steps c1') and c2') until the electrolyte mixture including the sodium chloride contained in the electrolyte tank is completely dissolved: Sub-step c1') transfer part of the solution contained in the mixing tank into the electrolyte tank, then Sub-step c2') transfer the solution contained in the electrolyte tank into the mixing tank, leaving the still solid constituents in the electrolyte tank;

Step d'): Stir and recirculate the solution by extracting it from a point in the mixing tank and reintroducing it at another point until a homogeneous liquid acid concentrate is obtained;

wherein Steps a') to c') can be performed in any order, Step a') preceding always Step c').

REFERENCE LIST

1 Facility
110 Mixing tank
111 Scale
112 Stirrer
113a Withdrawal line
113b Return line
114 Pump in the withdrawal line
115 Density meter
116 Transfer line to the buffer tank
117a Three-way valve
117b Three-way valve
117c Three-way valve
117d Three-way valve
120 Water tank
121 Water introduction line
122 Pump
130 Acid tank
131 Acid introduction line
132 Pump
140 Electrolyte tank
141 Inner bag
142 Cardboard box
143 Bag line
144 Connector
145 Filter
147 Electrolyte transfer line
147a Supply line
147b Extraction line
150 Sodium chloride tank
151 Hopper
152 Screw conveyor
153 Screw conveyor
160 Buffer tank

The invention claimed is:

1. A facility for manufacturing a predetermined quantity of a batch of liquid acid concentrate for hemodialysis machines wherein the facility comprises:

a mixing tank;
a water source connected to the mixing tank via a water introduction line;
an electrolyte tank containing a mixture of the electrolytes potassium and/or calcium and/or magnesium in exact quantities needed to manufacture the batch of liquid acid concentrate, wherein said mixture optionally further contains at most one part of acid and/or at most one part of sodium chloride needed for the manufacture of the batch of liquid acid concentrate, wherein the electrolyte tank is equipped with a single bag line allowing both the transfer of a solution from the mixing tank into the electrolyte tank, as well as the transfer of the solution from the electrolyte tank into the mixing tank, wherein the single bag line is equipped with a connector for connection to a withdrawal line used to transfer the solution from the mixing tank into the electrolyte tank and to a return line used to transfer the solution from the electrolyte tank into the mixing tank;

the withdrawal line leads from the mixing tank to the electrolyte tank to transfer part of the solution from the mixing tank into the electrolyte tank and the return line leads from the electrolyte tank to the mixing tank for transferring the solution contained in the electrolyte tank into the mixing tank, wherein the withdrawal line and the return line are one and the same line, two different lines, or a combination of the same and different lines;

a recirculation line;

at least one pump to convey solution in the withdrawal line, the return line, and the recirculation line;

an acid source connected to the mixing tank and configured to introduce the acid at a quantity needed for the manufacture of the batch into the mixing tank, taking into account the acid that is optionally already present in the electrolyte tank; and a sodium chloride source connected to the mixing tank, the sodium chloride source configured to introduce a solid sodium chloride at a quantity needed for the manufacture of the batch into the mixing tank, taking into account the sodium chloride that is optionally already present in the electrolyte tank.

2. The facility according to claim 1, wherein the mixing tank is equipped with a scale to determine by weighing the amount of water, acid and sodium chloride introduced into the mixing tank and/or to weigh the quantity of solution transferred from the mixing tank into the electrolyte tank, as well as the quantity of solution transferred from the electrolyte tank into the mixing tank.

3. The facility according to claim 1, wherein the mixing tank is equipped with stirring means.

4. The facility according to claim 3, wherein the stirring means is a stirrer with a mechanical drive.

5. The facility according to claim 1, wherein the facility is further equipped with
   a conductivity meter to measure the conductivity of the solution, wherein the conductivity meter is placed in the mixing tank or in the recirculation line;
   a density meter to measure the density of the solution.

6. The facility according to claim 1, wherein
   the water introduction line for introducing the water into the mixing tank, and/or the return line for transferring the solution contained in the electrolyte tank into the mixing tank, and/or the acid source and/or the sodium chloride source open into a top of the mixing tank; and/or
   an inlet of the withdrawal line for transferring a portion of the solution from the mixing tank to the electrolyte tank is located at a bottom of the mixing tank; and/or
   an inlet of the recirculation line is located at the bottom of the mixing tank and an outlet of the recirculation line is located at the top of the mixing tank.

7. The facility according to claim 1, wherein the facility is further equipped with
   a conductivity meter to measure the conductivity of the solution, wherein the conductivity meter is placed in the mixing tank or in the recirculation line;
   a density meter, placed in the recirculation line or in a bypass of the recirculation line, to measure the density of the solution.

8. The facility according to claim 1, further comprising a conveyor configured to convey the solid sodium chloride from the sodium chloride source to the mixing tank.

9. The facility according to claim 1, wherein the batch is from 100 liters to 4,000 liters.

10. The facility according to claim 1, wherein the batch is at least 100 liters.

11. The facility according to claim 1, further comprising:
   a buffer tank; and
   a conveying line that leads from the mixing tank to the buffer tank, wherein
   the conveying line is for transferring the batch of liquid acid concentrate from the mixing tank to the buffer tank.

* * * * *